US011510595B2

(12) United States Patent
Schwind et al.

(10) Patent No.: US 11,510,595 B2
(45) Date of Patent: Nov. 29, 2022

(54) TUBULAR SENSOR FOR THE DETECTION OF AN ANALYTE (75) Inventors: Karin Schwind, Schifferstadt (DE); Hans-Peter Haar, Wiesloch (DE); Otto Fuerst, Viernheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1104 days.

(21) Appl. No.: 12/611,579

(22) Filed: Nov. 3, 2009

(65) Prior Publication Data
US 2010/0113907 A1 May 6, 2010

Related U.S. Application Data (63) Continuation of application No. PCT/EP2008/055233, filed on Apr. 29, 2008.

(30) Foreign Application Priority Data

May 3, 2007 (EP) .................................... 07107436
Sep. 21, 2007 (EP) .................................... 07116982

(51) Int. Cl.
A61B 5/145 (2006.01)
A61B 5/1486 (2006.01)
A61B 5/00 (2006.01)

(52) U.S. Cl.
CPC ...... A61B 5/14532 (2013.01); A61B 5/14546 (2013.01); A61B 5/14865 (2013.01); A61B 5/6848 (2013.01); A61B 5/6849 (2013.01)

(58) Field of Classification Search
CPC ............ A61B 5/14532; A61B 5/14865; A61B 5/6848; A61B 5/150389; A61B 2562/125; A61B 2562/227; A61B 5/150511; A61B 5/6852; A61M 2230/201; C12Q 1/001; H01R 2201/12
USPC ........................ 600/309, 345, 347, 365, 372; 607/116–122
See application file for complete search history.

(56) References Cited

U.S. PATENT DOCUMENTS 5,286,362 A    2/1994 Hoenes et al.
5,299,571 A *  4/1994 Mastrototaro ................ 600/347
5,458,629 A * 10/1995 Baudino et al. .............. 607/116
5,488,768 A *  2/1996 Mar ..................... A61N 1/0563
                                                       228/173.5

(Continued)

FOREIGN PATENT DOCUMENTS

CA    2050677 C    3/1992
EP    0320109 A1   6/1989

(Continued)

OTHER PUBLICATIONS

English Translation of the corresponding PCT International Report on Patentability dated Nov. 5, 2009.

Primary Examiner — Christian Jang
Assistant Examiner — Karen E Toth
(74) Attorney, Agent, or Firm — Bose McKinney & Evans LLP (57) ABSTRACT An implantable sensor can be used for determining a concentration of at least one analyte in a medium, particularly in a body tissue and/or a body fluid. The implantable sensor can comprise a flexible, tubular sensor element. This sensor element has a tubular body on which at least two electrode rings are mounted for electrochemical determination of the concentration of the analyte.

27 Claims, 4 Drawing Sheets

(56) References Cited

U.S. PATENT DOCUMENTS

| | | | |
|---|---|---|---|
| 5,591,139 A | 1/1997 | Lin et al. | |
| 6,537,243 B1* | 3/2003 | Henning | A61B 5/1411 600/581 |
| 6,892,085 B2 | 5/2005 | McIvor et al. | |
| 2002/0035319 A1* | 3/2002 | Spehr | A61N 1/056 600/374 |
| 2002/0120186 A1* | 8/2002 | Keimel | A61B 5/14865 600/365 |
| 2003/0236562 A1 | 12/2003 | Kuzma | |
| 2004/0260166 A1* | 12/2004 | Merilainen | A61B 5/685 600/383 |
| 2005/0060855 A1* | 3/2005 | Davis | A61G 17/00 27/3 |
| 2005/0060885 A1* | 3/2005 | Johnson | A61B 18/1492 29/846 |
| 2005/0245799 A1* | 11/2005 | Brauker | A61B 5/14865 600/347 |
| 2005/0256557 A1* | 11/2005 | Wessman | A61N 1/056 607/116 |
| 2006/0025748 A1* | 2/2006 | Ye | A61B 5/14542 604/503 |
| 2006/0061253 A1* | 3/2006 | Van Gorkom | H01J 31/124 313/495 |
| 2006/0064149 A1* | 3/2006 | Belacazar | A61N 1/05 607/122 |
| 2006/0111768 A1* | 5/2006 | Wessman et al. | 607/116 |
| 2006/0224141 A1* | 10/2006 | Rush | A61B 5/0002 604/503 |
| 2006/0241366 A1* | 10/2006 | Falwell et al. | 600/374 |
| 2006/0253085 A1* | 11/2006 | Geismar | A61B 5/14532 604/272 |
| 2007/0027370 A1 | 2/2007 | Brauker et al. | |
| 2007/0027384 A1* | 2/2007 | Brister | A61B 5/14532 600/365 |
| 2008/0200897 A1* | 8/2008 | Hoss | A61M 5/14244 604/504 |
| 2008/0214916 A1* | 9/2008 | Yodfat | A61B 5/14532 600/347 |
| 2010/0256593 A1* | 10/2010 | Yodfat | A61M 5/14248 604/504 |

FOREIGN PATENT DOCUMENTS

| | | |
|---|---|---|
| EP | 0645160 A1 | 3/1995 |
| GB | 1465417 | 2/1977 |
| WO | 00/49940 A2 | 8/2000 |
| WO | 2006/124759 A2 | 11/2006 |

* cited by examiner

TUBULAR SENSOR FOR THE DETECTION OF AN ANALYTE

CROSS-REFERENCES TO RELATED APPLICATIONS

This application is a continuation of PCT Application No. PCT/EP2008/055233 filed Apr. 29, 2008, which claims priority to European Application Nos. 07107436.3, filed May 3, 2007, and 07116982.5, filed Sep. 21, 2007.

FIELD OF THE INVENTION

The invention relates to a subcutaneous sensor for determining a concentration of at least one analyte in a medium, particularly in a body tissue and/or a body fluid. The invention further relates to a sensor system and to a method for producing an implantable sensor. Such sensors or sensor systems are used particularly in the medical sector, for example for electrochemical determination of a concentration of blood glucose, triglycerides, lactate or other analytes.

DESCRIPTION OF THE RELATED ART

Determination of blood glucose concentrations and corresponding medication are an essential part of the daily routine of diabetics. The blood glucose concentration has to be determined quickly and simply several times a day (typically two to seven times) in order, if appropriate, to be able to take suitable medical measures. In many cases, medication is administered by means of automated systems, in particular by what are called insulin pumps.

So as not to restrict a diabetic's daily routine any more than is necessary, suitably portable devices are often employed which are intended to be easy to carry around and to operate, such that the blood glucose concentration can easily be measured, for example at the workplace or even during leisure time. Various portable devices are presently available on the market, some of them functioning with different measurement techniques and using different diagnostic techniques. A first measurement method is based, for example, on an electrochemical measurement technique, in which a blood sample which has been taken from the patient's body tissue, for example by perforating a layer of skin by means of a lancet, is applied to an electrode coated with enzymes and mediators. Corresponding test strips for electrochemical measurement methods of this kind are described in U.S. Pat. No. 5,286,362, for example. Other known measurement techniques use optical measurement methods which, for example, are based on the fact that the substance to be detected (analyte) can react with specific detection reagents, such that there is a change in the color of the reaction mixture. Systems for detecting color reactions of this kind, and therefore for detecting the corresponding analytes, are known from CA 2,050,677, for example.

The described detection methods therefore mainly involve a patient first taking a suitable sample of a body fluid to be examined (which is a blood sample or a urine sample for instance) and then examining it suitably by means of a test device. However, this method has various disadvantages. In the first place, this method is extremely complicated and entails several handling steps. Thus, for example, a lancet has to be provided and tensioned, a skin layer then has to be perforated by means of this lancet, a drop of blood thus produced then has to be applied to a test strip, and this test strip then has to be evaluated by means of a corresponding device. For many patients, particularly older people and children, these handling steps can often be carried out only with difficulty since the patients are restricted, for example, in terms of their motor ability and their visual acuity. Furthermore, these method steps can be carried out discretely only in a few cases, which means, for example, that the patient's privacy is protected only to an inadequate extent when carrying out a measurement at the workplace. Moreover, incorrect operation of the measurement method can easily lead to false measured values, in some cases with fatal consequences resulting from incorrect medication based on the measurement results.

The prior art therefore discloses systems which can be implanted into a body tissue and which, for example, supply measured values continuously. U.S. Pat. No. 6,892,085 B2, for example, discloses an encapsulated glucose sensor system comprising a glucose sensor and a protective encapsulation. In this case, three electrodes are provided, namely a working electrode, a counter-electrode and a reference electrode, which are applied on one side of a thin substrate. For easier implantation, this electrode arrangement is introduced into a hollow needle that is inserted into body tissue.

U.S. Pat. No. 5,591,139 also discloses an implantable microneedle system, by means of which substances can be taken from living tissue for diagnostic purposes. An etched three-dimensional substrate is used in this case.

US 2007/0027384 A1 describes systems and methods for continuous monitoring of analytes. Various embodiments of coaxial structures of implantable sensors are described in which various electrodes of electro-chemical sensors are coaxially superposed on one another and end in different axial areas, such that in each case an active surface of an electrode lies exposed. However, because of the different diameter of these coaxial electrodes, these individual electrode surfaces differ in terms of their properties and are limited in number. Although the coaxial design is described in US 2007/0027384 A1 as being particularly insensitive with respect to bending, in contrast to planar sensor constructions, the solid structure in itself entails a high degree of stiffness of the sensors, and bending may even alter the active electrode surface areas and thus greatly influence the measured values. US 2007/0027384 A1 alternatively proposes a rod-shaped structure in which spiral-shaped electrodes are wound around a rod-shaped base electrode. This structure has the disadvantage that the exact position of the individual electrodes may be undefined, since the spiral-shaped electrodes can move along a longitudinal axis of the sensors. Moreover, the number of the electrodes thus configured is limited, which has the result, for example, that an averaging of the measured values obtained from several electrodes can be done only with difficulty using this structure.

U.S. Pat. No. 5,299,571 also discloses a device for implantation of in vivo sensors. A flexible tube with a double inner lumen is used. One of these inner lumens receives a needle, which serves for the implantation and which can then be removed. The second inner lumen receives a sensor, which is in contact with the tissue via a window in the tube.

Overall, the implantable sensors known from the prior art are extremely complicated as regards their structure and their production. If it is assumed that these sensors are disposable sensors that can only be used for a short time (typically for about one week), then it is clear that the methods used in the sensors known from the prior art do not satisfy the requirements made of disposable articles.

Thus, for example, a complicated microstructuring method, in particular a lithographic method, is required to produce the sensor known from U.S. Pat. No. 5,591,139.

However, such methods are not compatible with the production of cost-effective disposable articles. Complicated structuring methods are also needed for producing the sensor known from U.S. Pat. No. 6,892,085 B2, since the electrode pads have to be carefully structured. In view of the small size of these electrodes, lithographic methods are likewise required for these, which again drives up the costs for producing such sensors.

The construction known from U.S. Pat. No. 5,299,571 is also technically complicated since, in addition to a tube with two inner lumens having to be produced, it is also necessary for a conventional sensor element, but one with miniaturized dimensions, to be inserted into one of these inner lumens.

Moreover, lithographic methods, in particular the etching of metal layers that is associated with these methods, are not always as reliable as is necessary for the production of medical products. In particular, it can happen that individual electrodes are still connected to one another by "bridges", such that the functionality of the sensors can easily be impaired or even completely prevented on account of production problems.

SUMMARY OF THE INVENTION

Illustrative embodiments of the sensor disclosed herein can be produced simply and cost-effectively by means of a reliable production method and can avoid the disadvantages of the sensors and methods known from the prior art. In particular, illustrative embodiments of the sensor described herein are intended to be easy to implant and well tolerated in the implanted state.

An implantable sensor is claimed which is suitable for determining a concentration of at least one analyte in a medium. This medium can in particular be a body tissue, for example subcutaneous tissue, and/or a body fluid. In addition to the aforementioned medical uses, further uses are conceivable, in particular uses in the field of continuous monitoring (CM) in different areas of medicine, natural sciences and technology. In addition to the field of medicine, such uses lie, for example, in quality control (for example in the food industry), in environmental analysis, or in other areas of technology or the natural sciences in which a concentration of an analyte has to be determined electrochemically.

The implantable sensor preferably comprises an implantation needle, and a flexible, tubular sensor element surrounding the implantation needle. Here, and in the text below, the term "tubular" is to be understood as meaning an element which has substantially the shape of a hollow cylinder with an inner lumen. The inner lumen is preferably arranged centrally, such that a symmetrical hollow cylinder is preferred. Moreover, an individual inner lumen is preferably provided, in contrast to the structure described in U.S. Pat. No. 5,299,571, for example, in which the actual planar sensor element is arranged not in the inner lumen of a hollow cylinder, but instead in a "pocket" that is separate from the central inner lumen. According to the invention, the symmetry of the sensor element is considerably improved by this means, and the sensor element can be made more flexible and less sensitive to bending. By virtue of the central arrangement of the inner lumen, the hollow cylinder does not constitute a simple casing of a sensor element but instead forms a carrier material of the sensor element. In this way, it is also possible to dispense with additional casing materials, and the entire structure can be greatly simplified.

Moreover, implantation or insertion of the sensor element into tissue layers is made easier with an atraumatic needle tip.

The wall of the hollow cylinder should in particular be flexible and extensible, for example so as to be able to be drawn onto the implantation needle and/or to avoid causing injuries in the body tissue. The wall of the hollow cylinder can therefore be particularly deformable, i.e. plastically and/or elastically, and can be substantially constant along a longitudinal axis of the hollow cylinder, which axis can assume a curved path, although it can also be provided with a varying thickness, for example with a thickness that varies by not more than 10% along the lengthwise extent of the tubular element. The cross section of the inner lumen is also preferably constant along the lengthwise extent of the tubular element, although it too can vary, for example by not more than 30%, and greater narrowing of the cross section may also occur particularly in the area of greater curvatures.

The tubular sensor element in turn comprises a flexible, tubular body. Here, "flexible" is to be understood as meaning a deformability of the body under the customary forces that occur in the implanted state, which is intended to avoid injuries of the surrounding tissue in the implanted state. This considerably increases the comfort for the patient. For example, the material used for the flexible tubular body can be a plastic material, for example a thermoplastic and/or elastomeric material, such as silicone, polyethylene, polyester or polyimide.

In an embodiment of an implantable sensor according to the invention, and in contrast to the sensor structure as disclosed in U.S. Pat. No. 5,299,571, no additional sensor element is inserted into the tubular body and in contact with the tissue fluid through a window, and instead this tubular body itself forms the basis for the sensor element. For this purpose, at least two electrode rings for electrochemical determination of the concentration of the analyte are mounted on the tubular body.

The term "electrode ring" is not to be understood necessarily as meaning that they are uniformly circular or form complete rings, even though complete electrode rings, i.e. electrode rings extending about a complete circumference of the tubular sensor element, are preferred. However, an "electrode ring" is to be understood as an electrode surface which extends at least partially about a circumference of the tubular sensor element, for example in contrast to electrode surfaces of purely planar configuration.

Thus, the cross section of the tubular body, and also of the tubular sensor element, can also deviate from a circle shape and can, for example, assume a polygonal shape. The electrode rings mounted circumferentially on the tubular body then also preferably assume these cross-sectional shapes.

In terms of their longitudinal extent too, these "rings" do not necessarily have to be rings with straight and mutually parallel borders extending along the circumference of the tubular body, and instead it is also possible to provide notched electrode rings, or electrode rings whose edges, in some areas, extend obliquely with respect to the axis of the tubular body.

As regards the extent of their closure around the circumferential surface, the electrode rings do not necessarily have to be completely closed, i.e. they do not necessarily extend around the full circumference of the tubular sensor element. For example, the electrode rings can also have one or more gaps. However, the electrode rings preferably extend around most of the circumference, i.e. preferably around at least 60% of the circumference, particularly preferably 80% of the circumference, and ideally around at least 95% of the circumference of the tubular sensor element, or even around the entire circumference (i.e. without a gap).

For the contacting of the electrode rings, electrically and/or galvanically insulated supply lines for the at least two electrode rings are embedded in the tubular body. These supply lines are preferably in the form of wires. During the production of the tubular body, these wires can be created for example by co-extrusion with the material of the body and/or can be incorporated into the body.

These supply lines are electrically connected to the supply lines preferably by electrical plated through-holes that extend at least partially through the body. When producing these plated through-holes, one or more vias are preferably first created in at least one material layer between the electrode rings and the supply lines. This via is then at least partially filled with at least one electrically conductive material. To produce the plated through-holes and vias, at least one of the following methods can be used for example: a mechanical drilling method, in particular a conventional drilling method; a laser drilling method; a laser ablation method; or an etching method. Other methods used in printed circuit board production are also conceivable. The conductive material for filling the vias can be, for example, at least one of the following materials: a metal; a conductive adhesive; a conductive paste, in particular a conductive paste with at least one binder material and at least a proportion of conductive particles, the conductive particles preferably being carbon particles, in particular microparticles or nanoparticles, metal particles or mixtures of these particles. Similar conductive materials or material combinations can also be used. Conductive pastes have proven particularly suitable, preferably conductive pastes with at least one binder material and at least a proportion of conductive particles. As the binder material, it is possible, for example, to use acrylic adhesives, which are preferably filled with conductive particles. Carbon particles have proven particularly suitable, in particular microparticles or nanoparticles. It is also possible to use metal particles or mixtures of said types of particles. Moreover, the pastes can additionally contain solvents, examples of possible solvents being ethylene glycol or propylene glycol derivatives (i.e. esters or ethers thereof), as are used in many pastes required in electrical engineering. Derivatives of propane-1,2-diol are preferred, because of the harmless degradation.

The nature and structure of the electrode rings can be adapted to the analyte that is to be detected. In particular, the electrode rings can comprise simple metal electrodes. Alternatively or in addition, the electrode rings can also be structured in such a way that they comprise in each case at least one electrically conductive contact ring (for example composed of a metal layer and/or of a conductive paste) directed toward the tubular body and in each case at least one function layer applied to the contact ring.

The at least two electrodes can comprise in particular at least one working electrode and at least one further electrode. The at least one further electrode can be operated, for example, as a counterelectrode and/or as a reference electrode. The at least one counterelectrode should in particular have a redox behavior that is the reverse of the redox behavior of the at least one working electrode. A counterelectrode and a reference electrode can also be designed as a common electrode, preferably as a common electrode whose electrode surface area is greater than the surface area of the at least one working electrode. The surfaces of the electrode rings can be adapted to the desired current densities.

The prior art discloses various examples for the use of electrode materials (i.e. both for the contact rings and also for the function layers) for electrochemical measurement methods. Thus, for example, electrodes can be coated with enzymes or other chemical adjuvants which are specific to the analyte to be detected. By way of example, for detecting glucose it is possible to use glucose oxidase (GOD), which converts glucose into gluconolactone. The charge carriers released in the process are detected. To permit this detection, overvoltage-reducing materials are generally used, which serve as charge mediators between the function layer and the contact rings. Many of these overvoltage-reducing materials are harmful to health, however. In particular, mediators along with the enzymes have proven to be toxic, such that it is in many cases necessary to immobilize these overvoltage-reducing materials for use in implantable sensors. For example, a covalent bonding to the contact rings and/or to a layer of the electrode, for example a metal layer, can be effected for immobilization purposes. A second possibility involves integrating overvoltage-reducing material into an insoluble layer that is insoluble in a fluid, in particular a body fluid, surrounding the implantable sensor in the implanted state. This can be done, for example, by using manganese dioxide, which can be used in paste form as a constituent of the function layers and which is then substantially insoluble after drying.

The mediators can be nitrosoanilines, hexacyanoferrate, ferrocenes or other known mediators. Other materials can also be used besides manganese dioxide.

Besides the described configuration of the electrode ring or electrode rings functioning as working electrode, the at least one electrode ring or electrode rings functioning as reference electrode and/or as counterelectrode can also be configured in various ways. Thus, the at least one reference electrode should have an electrode system with an electrochemical potential that does not change, or changes only inappreciably, in a working range of the implantable sensor, when operated without current. This ensures that the reference electrode acts as an actual reference whose potential can be used for comparison of the electrochemical potential of the at least one working electrode.

In principle, a plurality of materials and/or material combinations can be used for the reference electrode. A silver/silver chloride (Ag/AgCl) electrode system has proven particularly advantageous. Other electrode systems can also be used in principle, but are less common, for example $Hg_2Cl_2$ electrode systems.

Depending on the wiring, one or more electrode rings designed as a working electrode can interact with one or more electrode rings designed as a reference electrode. In addition, depending on the wiring, this interaction can also involve one or more electrode rings designed as counterelectrodes. Accordingly, it is preferable if the implantable sensor has a number of electrode rings constituting an integral multiple of three or an integral multiple of two. In this case, the groups of electrode rings belonging together form individual sensors in each case preferably independent of one another. The total number of electrode rings preferably lies in the range of between (and including) 2 and 21, and particularly preferably in the range of between (and including) 6 and 15.

The at least one counterelectrode can also be configured in a large number of different ways. In this case, however, it should be ensured that the at least one counterelectrode has an opposite redox behavior to a redox behavior of the at least one working electrode with respect to the surrounding fluid. Therefore, if an oxidation takes place at the working electrode, a reduction should take place at the counterelectrode, and vice versa. In principle, pure metals can be used as counterelectrodes, for example platinum. In this case, the additional function layer on the conductive contact ring (in this case a platinum ring) could be omitted. This has the disadvantage, however, that a gas formation, for example a formation of hydrogen or oxygen, typically occurs at metal electrodes of this type. A gas formation of this kind is undesirable, however, when the sensor has been implanted in the body tissue. In this respect, it is once again advantageous here if an electrode system, in particular a redox electrode system, is used in which gas formation is avoided. In particular, an Ag/AgCl electrode system can again be used here too. By way of example, AgCl is reduced in this case. It is evident from this that the counterelectrode is consumed during the operation of the sensor. If the counterelectrode has been fully consumed, gas formation once again often takes place, such that the implantable sensor generally has a limited lifetime in operation. Accordingly, it can also be advantageous if the at least one electrode ring designed as counterelectrode is made larger in terms of its surface area than the electrode ring or electrode rings designed as working electrode.

The way in which the electrode rings or contact rings and/or function layers are applied can be adapted in each case to the materials used. In particular, this application should be effected in such a way that the electrode rings or the component layers thereof are applied in a structured manner, i.e. not across a large surface area but instead already substantially in their desired ring shape. If, for example, pure metals are used as electrode materials, then it is possible, for example, to use film methods (e.g. lamination) or wet-chemical methods, physical application methods (physical vapor deposition, PVD), for example vapor deposition or sputtering, or chemical application methods (chemical vapor deposition, CVD). Manganese dioxide or carbon ($MnO_2$/C) can be applied, for example, as a coating, for example as a paste coating or as a galvanic coating. For this purpose, various paste coating methods known to a person skilled in the art can be used, for example screen printing, blade coating, nozzle coating, inkjet methods, piezo or thermo jet methods, contact printing methods (for example pad printing methods, offset printing methods) or electrostatic printing methods. In this case, for example, an enzyme (for example GOD) can already be mixed with the paste, such that enzyme and manganese dioxide can be applied in one step. Alternatively, manganese dioxide can also be applied first, whereupon the enzyme is applied in a subsequent step, for example dispensed thereon or applied by another wet-chemical step. It is generally preferable if, when applying the contact rings and/or the function layers, at least one of the following methods for structured application of a layer is used: a laminating method; a spray-on method; an inkjet method, in particular a piezo or thermo jet method; an offset method; or an electrostatic printing method.

Accordingly, the other electrode rings or other electrode layers are also applied by corresponding methods, for example spray-on methods, inkjet methods, or the other methods that have been mentioned, or further methods or combinations of methods. Typical layer thicknesses of the electrode rings lie, for example, in the region of 10 µm, but may also be in the range of 100 µm to several hundred µm. Thinner electrode layers are also conceivable.

Besides the described methods for applying the electrode rings, in which the electrode rings are applied directly onto the tubular body, it is also possible to use indirect application methods (as has already been indicated above by the laminating method). For example, when applying the contact rings and/or the function layers, individual layers or a plurality of the layers can be applied at least partially onto a flexible carrier substrate, after which the flexible carrier substrate is applied to the tubular body. For example, this application can be done by adhesive bonding and/or by using additional retaining elements or by an interference fit.

Since the electrode rings and materials commonly used for the function layers may in some cases be toxic and, for example, act as cytotoxins, it is preferable if the electrode rings, on the side directed away from the tubular body, are at least partially surrounded by at least one membrane layer. The at least one membrane layer should be at least partially permeable to the at least one analyte that is to be detected. For example, the at least one membrane layer can have a permeability to glucose, lactate, triglycerides and/or other analytes. However, the at least one membrane layer should advantageously be impermeable to the adjuvant chemicals used in the electrochemical measurement method, for example the enzymes which are applied to one or more of the electrodes (for example glucose oxidase). The membrane layer thus also ensures that these adjuvant chemicals cannot penetrate into the body tissue and cause damage there.

The at least one membrane layer can, for example, enclose the area in which the electrode rings are arranged. For example, the at least one membrane layer can comprise a polymer or be a polymer, for example a polyurethane. A multi-layer membrane structure is also possible. For example, the membrane layer can be applied once again by wet-chemical methods, for example immersion methods and/or spray-on methods, or by other known coating methods.

The implantation needle can be a component part of the sensor or can be stored as a separate element, in order to be inserted subsequently into the tubular sensor element immediately before implantation. After implantation of the sensor into the body tissue, the implantation needle is preferably withdrawn at least partially from the tubular body and is therefore preferably mounted slidably in this tubular body. Instead of a complete withdrawal, an only partial withdrawal is also possible, for example followed by bending off the implantation needle.

To avoid causing irritation during implantation, while at the same time ensuring easy implantation, it has proven advantageous to use an acupuncture needle as implantation needle, in particular an acupuncture needle with a diameter of between 0.4 mm and 0.7 mm. However, other diameters are also possible, for example diameters of between 0.2 mm and 0.35 mm. An implantation needle is preferably used which has an atraumatic tip, i.e. a tip without sharp edges, which can be seen for example in U.S. Pat. No. 5,299,571. Alternatively or in addition, the needle can also have a tip with a biocompatible, enzymatically degradable material which reacts with the body tissue and/or with a body fluid in such a way that in this case too the tip becomes at least partially rounded after implantation into the body tissue. Alternatively or in addition, it would be possible for it to be rounded by application of heat if a material were used that becomes at least partially rounded under the effect of body temperature.

The tubular body preferably has a length of between 3 mm and 50 mm, in particular of between 10 mm and 25 mm, and particularly preferably of 18 mm. Tubular bodies with an external diameter of between 0.3 mm and 1.5 mm, for example of between 0.5 mm and 1.5 mm, and particularly preferably of 0.8 mm, are preferably used. In accordance with the external diameter of the tubular body and the external diameter of the acupuncture needle, wall thicknesses of between 0.05 mm and 0.4 mm are preferred, particularly wall thicknesses of 0.2 mm. Such wall thicknesses still permit the use of extrusion methods and co-extrusion methods, for example, while at the same time allowing the supply lines to be embedded and ensuring the electrical insulation of these supply lines.

In the direction of their extent along the sensor axis, the electrode rings are preferably small compared to the length of the tubular body. As a result, they are preferably not subject to the limitations which affect planar sensors upon bending, on account of the electrodes applied to these sensors, which favors a high degree of flexibility and bendability of the planar sensor. In the longitudinal direction (i.e. in a direction parallel to the sensor axis), the electrode rings can, for example, have a width which is between 1% and 10% of the length of the tubular body, particularly preferably in the region of 5%. Instead of the total length of the tubular body, the interaction length of the sensor could also be used, i.e. that part of the tubular sensor which, after implantation, is arranged within the tissue. Alternatively or in addition, the width of the electrode rings can also preferably be regarded as a multiple of the diameter of the tubular body and is preferably between 20% and 200%, particularly preferably 100%, of the diameter.

Moreover, the electrode rings are preferably arranged in such a way that they have a spacing which is likewise preferably in the range of between 1% and 10%, particularly preferably 5%, of the length of the tubular body. Given in multiples of the diameter of the tubular body, the preferred spacing of and between adjacent rings is between 20% and 200%, and particularly preferably 100%, of the diameter of the tubular body.

In principle, the widths of the electrode rings and their spacings can be chosen individually, that is to say individually for each electrode ring, for example different than the other electrode rings. However, it is also, possible to alternatively choose an equidistant arrangement of the electrode rings and, alternatively or in addition, also a uniform width. Moreover, the electrode rings preferably all have an identical diameter (for example internal diameter), at least within the manufacturing tolerances, but in principle they can also be designed differently in terms of their diameters. For example, the diameter can correspond substantially to the external diameter of the sensor element. The electrode rings preferably do not have any overlapping in the direction of the longitudinal axis of the sensor element, as is the case in the coaxial structure in US 2007/0027384 A1, for example. In this way it is possible to obtain a highly symmetrical sensor structure in which, even in the event of slight bending, there are no changes in the electrode surfaces. The number of electrode rings can be chosen such that a multiplicity of measurement points can be interrogated along the sensor axis, with the result that it is also possible to calculate local differences in concentration in a simple manner. For example, ten or more electrode rings can be provided. In this way, the structure advantageously differs, for example, from the spiral-shaped electrode structure which is described in US 2007/0027384 A1 and which does not permit such a configuration.

The width of the electrode rings is preferably configured such that the entire width of these rings can be used electrochemically as an active surface for the electrode rings. In this way, the electrode rings again differ from the coaxial structure described in US 2007/0027384 A1. The use of the whole of the electrode rings as an active electrode surface has the effect that, even in the event of bending of the sensor element, there are no significant changes in the active electrode surfaces. Each electrode ring preferably has its own electrical lead or contact, such that the electrode rings can be well separated from one another galvanically. This means that no electrochemical interactions or even short-circuits occur between the individual electrode rings, as is possible in the coaxial structure described in US 2007/0027384 when the separating layers become wet.

At an end of the sensor element directed away from the tip of the implantation needle, electrical contacts can be provided for the contacting of the electrode rings or can be created during the production of the sensor element. These electrical contacts can be designed similarly to the above-described contact rings, such that, for example, a separate electrode contact ring is provided to each supply line. For the connection between the supply lines and the electrical contacts, reference may be made, for example, to the above-described methods concerning the connection between the electrode rings and the supply lines. For example, it is once again possible in the first instance to create vias, which are then completely or partially filled with an electrically conductive material.

As an alternative or in addition to the use of individual contacting rings for each supply line, the contacts can also be formed on a common, for example segmented connector contact ring onto the surface of the sensor element. In order to feed the electrical contacts electrically with signals or to capture corresponding measured signals from these, conventional methods can be used, for example methods that are known from display technology (for example conductive rubber strips, anisotropically conductive plastics, flex connectors or the like).

In order to close off the needle-tip end of the supply lines extending along the longitudinal axis of the tubular sensor element in the tubular body, the end of the sensor element directed toward the tip of the implantation needle can additionally be closed off with an electrical insulation, which separates the individual supply lines from one another and from the body tissue. The electrical insulation can comprise an insulating coating, for example. To apply this insulation or coating, it is again possible to use spray-on methods and/or immersion methods, or other methods too.

In contrast to the known implantable sensor systems described above, the implantable sensor and the described method for its production are distinguished by the use of simple and inexpensive method steps. In this way, the sensors can be produced inexpensively. At the same time, however, the possible redundant design of the electrode rings and the possible simultaneous use of several independent sensor units on one and the same tubular sensor element has an extremely positive effect on the reliability of the measurement signals. Local differences in concentration can be determined, and the long-term stability of the sensor systems can be greatly improved.

The implantable sensor can in particular be used in a sensor system according to the invention which, in addition to one or more of the above-described implantable sensors, also comprises, in one of the described embodiments, an actuation and evaluation unit. The latter is electrically connected to the electrode rings and is configured so as to carry out an electrochemical measurement for determining the concentration of the analyte. For this purpose, the actuation and evaluation unit can have corresponding voltage sources and/or current sources and also devices for measuring voltage and/or current (in each case one or more thereof). It can also include additional elements, for example evaluation elements, for example a microcomputer, operating elements and output elements, for example a display. Actuation and evaluation units of this kind are known to a person skilled in the art, except for the fact that in the present case, by analog means, and depending on the design of the sensor element, the signals from more than one group of electrode rings belonging to each other are intended to be processed.

The sensor system can in particular be designed such that, as has been described above, at least one of the electrode rings is connected as working electrode, and at least one electrode ring as counterelectrode and/or as reference electrode. Alternatively or in addition, separate electrode rings can also be provided as reference electrode and counterelectrode. Preferably, the electrode rings are each coupled alternately, such that, for example, a counterelectrode is followed by a reference electrode and then a working electrode, then once again a counterelectrode, a reference electrode and a working electrode, and so on. If only two types of electrode rings are used, it is possible, for example, for a working electrode to be followed by a counterelectrode, and then once again a working electrode and a counterelectrode, and so on. The latter configuration is preferred in particular in an arrangement in which an alternating current measurement method is exclusively used. Alternative embodiments are also conceivable, however, for example embodiments in which several sensor units share a reference electrode and/or counterelectrode.

In this way, by means of one or more of the implanted sensors, it is possible to assemble a sensor system which provides the patient with measurement data, for example concerning a blood glucose concentration, in a reliable way and consistently over quite a long period of time (for example a week). The sensor system can also forward this information to other suitable devices or persons, for example by data transfer to a computer system and/or by data transfer to a medication system (for example an insulin pump). The system is inexpensive to produce and its operation is extremely reliable.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE SEVERAL VIEWS OF THE DRAWING

Further details and features of the invention will become apparent from the following descriptions of the illustrative embodiments in conjunction with the claims. In this case, the respective features can be realized singly or in combination with one another. The invention is not restricted to the illustrative embodiments.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Figure 1:
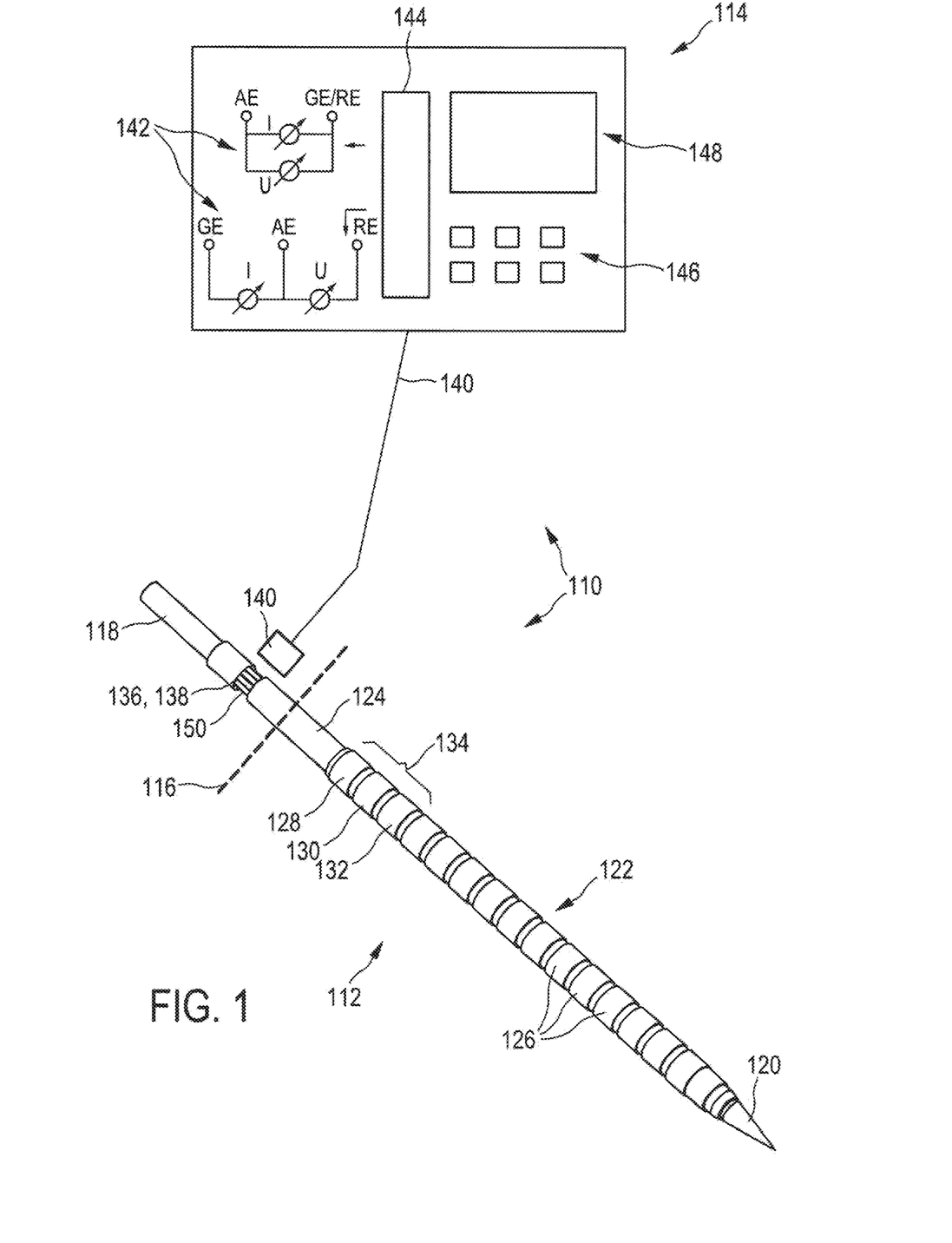
FIG. 1 shows an illustrative embodiment of a sensor system according to the invention.

In FIG. 1, an illustrative embodiment of a sensor system 110 for determining a concentration of at least one analyte in a medium is shown in a highly schematic representation. The sensor system 110 comprises an implantable sensor 112 and an actuation and evaluation unit 114 connected to the implantable sensor 112.

It is assumed below, without limiting the scope of the invention, that the implantable sensor 112 is a glucose sensor that can be implanted in a body tissue. In FIG. 1, the depth of implantation is indicated symbolically by a skin line 116. The implantable sensor 112 is inserted into the body tissue from its tip all the way to this skin line 116. The implantation needle 118 is removed after the implantation.

In this example, the implantable sensor 112 comprises, as central element, an implantation needle 118. In this illustrative embodiment, this implantation needle 118 is designed as an acupuncture needle and has an atraumatic needle tip 120, which has the shape of a pencil tip. It will be seen that this atraumatic needle tip 120 has no additionally sharp edges that could destroy surrounding tissue.

A flexible, tubular sensor element 122 is mounted circumferentially on the implantation needle 118, in such a way that the atraumatic needle tip 120 at the implantation end of the implantation needle 118 protrudes from the tubular sensor element 122. The implantation needle 118 is mounted slidably in the tubular sensor element 122, such that, on the one hand, safe implantation can be carried out, while on the other hand, after the implantation, the implantation needle 118 can be withdrawn from the tubular sensor element 122. Then, only the tubular sensor element 122 remains within the tissue, i.e. to the right of and below the skin line 116 in FIG. 1. Alternatively, the implantation needle 118 can also be withdrawn only partially from the tubular sensor element 122, in order then to be partially bent off, for example.

The tubular sensor element 122 typically has a flexible, tubular body 124. Electrode rings 126 are mounted circumferentially on this tubular body. These electrode rings 126 are suitably functionalized in order to form in each case a counterelectrode 128, a reference electrode 130 and a working electrode 132. Thus, in this illustrative embodiment, three electrode rings 126 together form an individual sensor 134, and the individual sensors 134 of the tubular sensor element 122 can in principle be actuated and evaluated independently of each other. Thus, in this illustrative embodiment according to FIG. 1, the total number of the electrode rings 126 forms an integral multiple of three (in this case 15 electrode rings are provided).

The sequence, number and arrangement of the electrode rings 126 can deviate from the illustrative embodiment shown in FIG. 1. For example, reverse sequences can also be used, for example working electrode/reference electrode/counter electrode. Other arrangements are also conceivable.

As an alternative to the three-electrode individual sensors 134 shown in FIG. 1, embodiments can also be used in which only two electrode rings 126 form an individual sensor 134. In this case, the total number of the electrode rings 126 would preferably be a multiple of two. This illustrative embodiment would be particularly suitable for a measurement method that uses alternating currents and that only requires in each case a working electrode and a counterelectrode or a combined counterelectrode/reference electrode.

At an end of the tubular sensor element 122 directed away from the tip 120, the electrode rings 126 are contactable by electrical contacts 136, which in this illustrative embodiment are arranged on a connector contact ring 138, and they are contacted by a corresponding electrical connection 140 and are connected by the electrical connection 140 (for example a cable or a wireless connection) to the actuation and evaluation unit 114.

The actuation and evaluation unit 114 is shown only symbolically and comprises a measuring device 142 and a control unit 144 (for example a microcomputer and/or additional electronic components), operating elements 146, and one or more output units, for example a display 148. All of the components are only shown schematically and are in principle known from the prior art. The measuring device 142 is equipped with various regulating and measuring units in order, for example, to measure and/or regulate currents I and voltages U between the electrodes (AE: working electrode, GE: counterelectrode, RE: reference electrode), such that electrochemical measurements known to a person skilled in the art can be carried out for determining the glucose concentration.

The actuation and evaluation unit 114 or the measuring device 142 and the control unit 144 can also have other functions, for example an at least partial evaluation and/or storage of the measurement data obtained or a graphic presentation and/or a database function. It is also possible to effect "intelligent" actuation and evaluation of the individual sensors 134, such that, for example, instead of being actuated and evaluated in parallel, they are instead actuated and evaluated one after another. In a multiplexing method of this kind, it is also possible, for example, for an individual sensor 134 to be used while adjacent individual sensors 134, or just individual adjacent electrode rings 126, are subjected to an electrical potential such that they shield the individual sensor 134 being used ("guard ring" function).

Figure 2A:
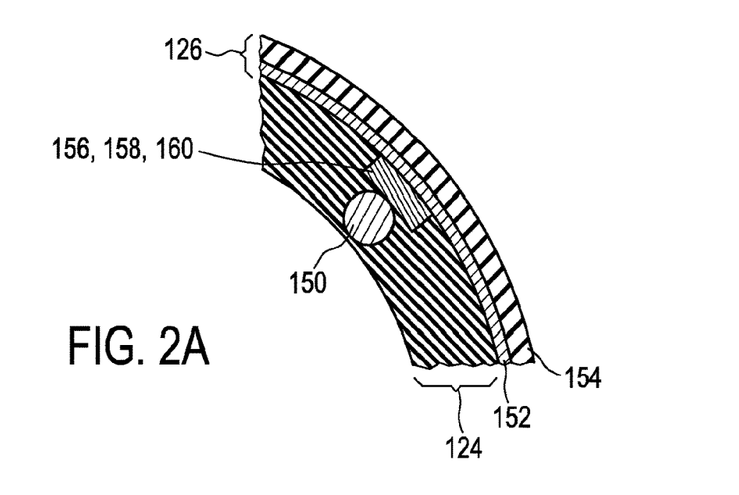
FIGS. 2A and 2B show different views of an illustrative embodiment of the contacting of the electrode rings.
Figure 2B:
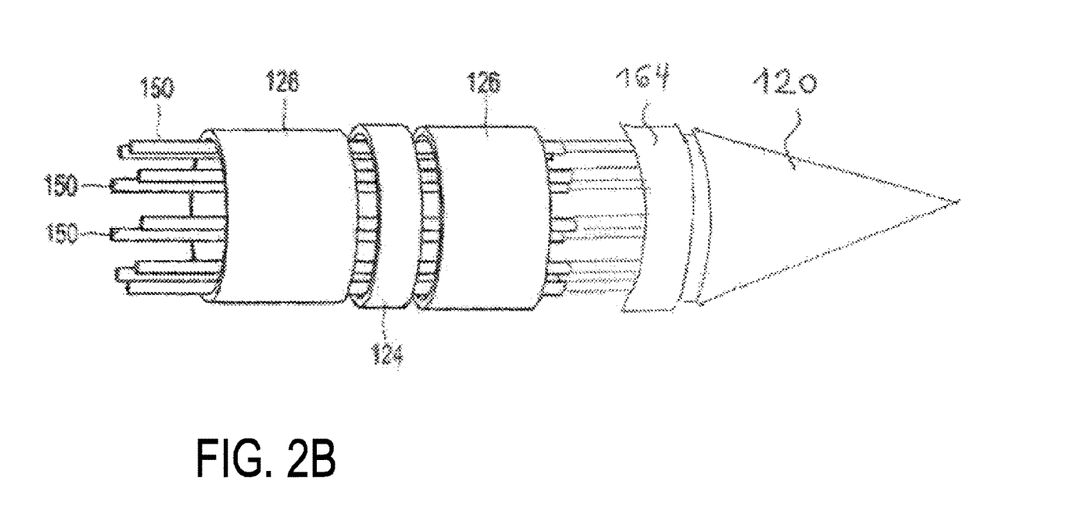

The structure and mode of function of the electrode rings 126 are shown schematically in FIGS. 2A and 2B.

It will be seen from the partial cross-sectional view in FIG. 2A that wires 150 are let into the tubular body 124 in the axial direction (i.e. parallel to the implantation needle 118). As is explained in more detail below, these wires 150 can be produced, for example, by co-extrusion with the tubular body 124, are arranged more or less equidistantly in the tubular body 124, and are electrically and galvanically insulated from one another.

The electrode rings 126 are then mounted on the tubular body 122. In the illustrative embodiment shown in FIGS. 2A and 2B, these electrode rings 126 each have two layers, namely an electrically conductive contact ring 152 and at least one function layer 154 applied on the contact ring 152. For example, the conductive contact ring 152 can be constructed using a conductive paste, which is applied in annular formation onto the tubular body 124. The function layer or function layers 154 are adapted to the respective function of the electrode ring 126 and have already been partly described above. To construct a working electrode, for example, manganese dioxide, a buffer and an enzyme can be contained in the function layer 154. To construct a reference electrode, silver and silver chloride particles, for example, can be contained in the function layer 154. A counterelectrode may, for example, not contain any function layer 154 (in which case the electrode ring 126 is then composed only of the contact ring 152), or, for example, a similar structure as for the reference electrode can be used.

In order to electrically connect the contact ring 152 to a wire 150 lying under same, it is preferable, before application of the contact ring 152, to first of all drill or cut a via 156 into the uppermost layer separating the wire 150 from the surface of the tubular body 124. As has been described above, mechanical methods or laser ablation methods can, for example, be used for this purpose. This via 156 can then be at least partially filled with an electrically conductive material 158. The contact ring 152 is then placed onto this electrically conductive material 158. The introduction of the electrically conductive material 158 and the production of the contact ring 152 can also take place in one and the same operating step since, for example, a conductive paste is used in both stages.

Then, for example, the contact ring 152 and/or the electrically conductive material 158 can be hardened, in order thereafter to apply the function layer 154 in a similar method. It will be noted that, instead of the simplified structure shown, a more complex, multi-layer structure is also possible.

The perspective view in FIG. 2B shows how the electrode rings 126 circumferentially enclose the framework of the wires 150, which in this case are uniformly distributed. The tubular body 124 is depicted only in part here, in order to show that the individual electrode rings 126 are electrically insulated from one another. Alternatively or in addition, it is also possible for additional insulations to be provided between the individual electrode rings 126 along the longitudinal axis of the implantable sensor 112, for example in the form of additional insulating rings between these electrode rings 126, which for example also facilitate the application of the individual electrode rings and their insulation from one another.

In this way, for example, each of the electrode rings 126 can be allocated a specific wire 150, by electrode ring 126 and wire 150 being connected to each other by way of the plated through-hole 160. On the electrical contacts 136 at the end of the tubular sensor element 122 directed away from the tip 120 (see FIG. 1), it is again possible to provide connector contact rings which are connected, for example, to in each case one of the wires 150.

Alternatively, the connector contact ring 138 can also be produced simply by exposing the wires 150 in this area, once again by removing the material layer of the tubular body 124 between the Wires 150 and the surface of the tubular body 124. For example, mechanical methods can once again be used for this removal, or, for example, a laser ablation method.

For the contacting of the individual wires 150, it is then possible, for example, to use methods which are known from display technology for example, such as flex connectors, conductive rubber strips or zebra connectors that are wound around the tubular body 124. For this purpose, the electrical connection 140 can also be designed, for example, as an annular element which is pushed onto the connector contact ring 138 from that end of the tubular sensor element 122 directed away from the tip 120. For allocating the individual electrode types and wires, it is possible, for example, for the wires 150 to be connected in a defined sequence to the electrode rings 126. Allocation would also be conceivable in which a revolver-like rotation mechanism is integrated in the electrical connection 140 or at a remote site in order to perform allocation only when the individual sensor 12 has been implanted. Electronic allocation is also conceivable.

Figure 3:
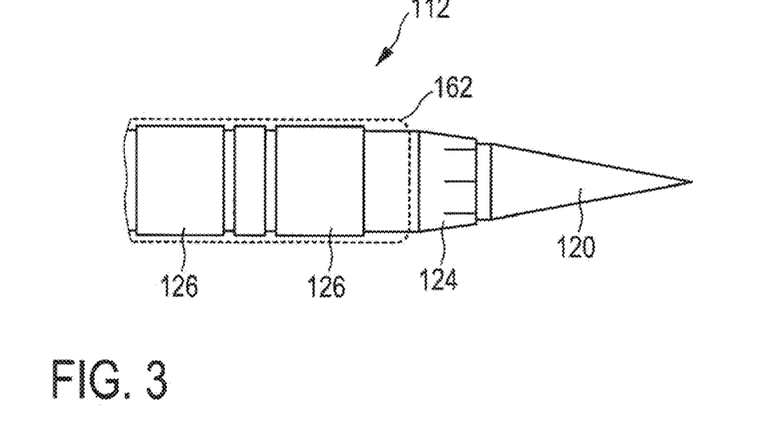
FIG. 3 shows a first illustrative embodiment of a tip of an implantable sensor.
Figure 4:
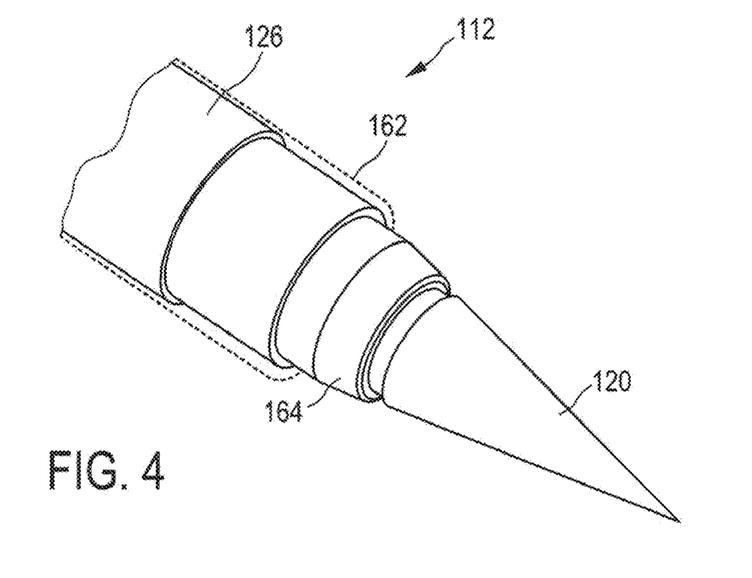
FIG. 4 shows a second illustrative embodiment of a tip of an implantable sensor.

FIGS. 3 and 4 show two different embodiments of the tips of the implantable sensor 112. It will be noted here (although this is not shown in FIG. 1) that the area of the tubular sensor element 122 where the electrode rings 126 are mounted is preferably additionally surrounded by a biocompatible membrane 162 permeable to the analyte (for example glucose). This membrane can, for example, be a polymer membrane and can serve to protect the surrounding tissue from toxic constituents of the electrode rings 126, and it can also deliberately limit a flow of current in the electrochemical measurement method. The membrane layer 162 can, for example, be applied in an immersion method or spray-on method.

The two illustrative embodiments of the implantable sensors 112 according to FIGS. 3 and 4 differ mainly in that, in FIG. 3, the end of the tubular body 124 directed toward the needle tip 120 lies free. In some circumstances, this embodiment has the disadvantage that wires 150 in this area either come into contact with the implantation needle 118 or, if unprotected, with the surrounding body tissue, in which case, for example, electrochemical reactions could be triggered, resulting in possible distortion of the measurement results of the electrochemical determination of the analyte concentration. By contrast, in the embodiment according to FIG. 4, the end of the tubular sensor element 122 directed toward the implantation needle 118 is covered by an insulating coating 164. For example, this can once again be easily done on a large scale by an immersion method or spray-on method. In this way, the ends of the wires 150 are also safely insulated from one another, from the implantation needle 118 and from the surrounding body tissue.

The implantable sensor 112 according to the above-described illustrative embodiments can be easily and inexpensively produced on a large scale and with high operational capacity. This simple production is an essential condition for use as a disposable sensor that can be discarded after a period of use of several hours or days.

Figure 5:
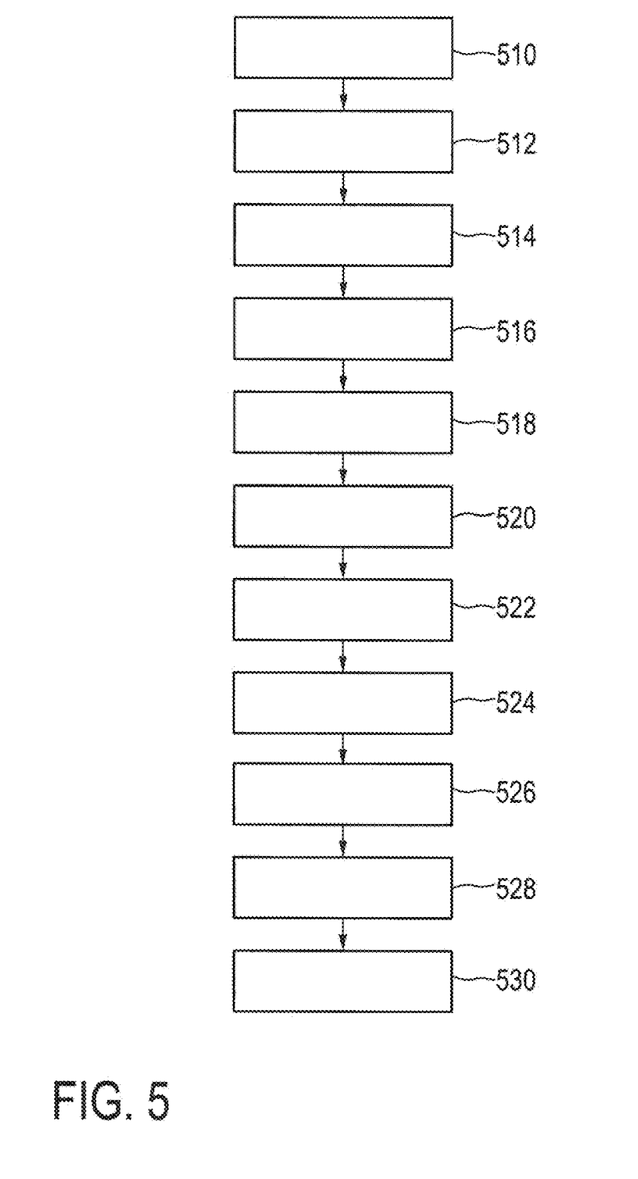
FIG. 5 shows a schematic flowchart of an illustrative embodiment of a method according to the invention for producing an implantable sensor.

FIG. 5 is a schematic representation of a possible illustrative embodiment of a production method for producing the implantable sensor 112. It will be noted that the method steps shown should preferably but not necessarily be carried out in the sequence shown, that individual or several method steps can also be carried out independently of one another, i.e. at the same time or overlapping in time, and that individual method steps can also be carried out repeatedly.

In a first method step 510, the tubular body 124 is produced. As has been explained above, this step can be carried out, for example, by co-extrusion of the tubular material with the wires 50. For example, the tube itself can have an external diameter of 0.8 mm and a wall thickness of 0.2 mm. For example, 9 to 15 wires can be embedded in the tube.

Then, in method step 512, the vias 156 are produced. These are then filled with the electrically conductive material 158 in method step 514.

The contact rings 152 are then applied in method step 516. As has been described above, this can be done, for example, by a pad transfer method (with a large roll on a small cylinder), by an offset printing method, by a jet method (for example a piezo method or other jet methods, such as a method in which a jet is generated by a mechanical impulse on a capillary), by an electrostatic method, by an electrospray method (such as is known from the aluminum coating industry for example) or by a xerox method.

An alternative method of producing the contact rings 152 or the entire electrode rings 126 is one in which they are prepared on a flat, flexible carrier. This flat carrier permits the use of simple, large-area production methods which are usually carried out on planar substrates. These flat carriers can then be mounted around the tubular body 124. For example, the flexible, flat carrier can comprise a flat carrier tape on which the required number of electrode strips is placed. This flat carrier tape can then be cut to the correct size, for example, and affixed as an elongate "label" to the hollow cylinder of the tubular body 124. The contacting of the contact rings 152 and electrode rings 126 produced in this way can again be carried out in the manner described above, that is to say, for example, by subsequent formation of a via 156, filling with electrically conductive material 158, and then hardening.

The production methods can also be combined, for example by the conductive layers being created on a flat, separate carrier material and then being applied to the tubular body 124, in order to thereafter apply the function layers 154 to the contact rings 152.

The application of the function layers 154 is shown symbolically in FIG. 5 by reference number 518.

Thereafter, in method step 520, the tubular element that has been produced in this way is cut to the length needed for the tubular sensor element 122. For example, sections measuring 18 mm in length can be cut out.

Thereafter, in method step 522, the sensor element is insulated, which, as has been described above, can be done, for example, by immersion in an insulating coating 164.

The connector contact ring 138 is produced in method step 524. As has been described above, this can be done, for example, by at least partial exposure of the wires 150. Other methods have also been described above.

In step 526, at least part of the tubular sensor element 122 (particularly preferably the part on which the electrode rings 126 are located) is coated with the analyte-permeable and biocompatible membrane layer 162.

Thereafter, in method step 528, a control step can be performed in which, for example, a basic check of the function of the tubular sensor element 122 is made.

Thereafter, in method step 530, the implantation needle 118 can be inserted into the tubular body 124. In order to avoid contamination of this needle during the production, this insertion is preferably carried out only after the tubular sensor element 122 has been produced. During the production of the tubular sensor element, another rod-shaped support element can be inserted instead of the needle into the inside of the tubular body 124 and later replaced by the implantation needle 118.

| List of reference numbers | |
|---|---|
| 110 | sensor system |
| 112 | implantable sensor |
| 114 | actuation and evaluation unit |
| 116 | skin line |
| 118 | implantation needle |
| 120 | needle tip |

-continued

| List of reference numbers | |
|---|---|
| 122 | tubular sensor element |
| 124 | tubular body |
| 126 | electrode rings |
| 128 | counterelectrode |
| 130 | reference electrode |
| 132 | working electrode |
| 134 | individual sensor |
| 136 | electrical contacts |
| 138 | connector contact ring |
| 140 | electrical connection |
| 142 | measuring device |
| 144 | control unit |
| 146 | operating elements |
| 148 | display |
| 150 | wires |
| 152 | contact ring |
| 154 | function layer |
| 156 | via |
| 158 | electrically conductive material |
| 160 | plated through-hole |
| 162 | membrane layer |
| 164 | insulating coating |
| 510 | producing the tubular body |
| 512 | producing the vias |
| 514 | filling the vias |
| 516 | applying the contact rings |
| 518 | applying the function layers |
| 520 | cutting |
| 522 | insulating the end of the sensor element |
| 524 | creating the connector contact ring |
| 526 | coating with membrane layer |
| 528 | function control |
| 530 | inserting the implantation needle |

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. An implantable sensor for determining a concentration of at least one analyte in a medium, the implantable sensor comprising a flexible, tubular sensor element, the tubular sensor element defining a longitudinal sensor axis, and the tubular sensor element comprising a flexible, tubular body and a plurality of electrode groups wherein each electrode group includes at least two electrode rings adapted for electrochemical determination of the concentration of the analyte; and wherein each of the electrode rings of each electrode group is mounted on the tubular body and is longitudinally spaced apart from each of the other electrode rings mounted on the tubular body, and wherein electrically and/or galvanically insulated supply lines each having an embedded length that extends from proximate an end of the tubular body opposite from an implantation end to a respective one of the electrode rings are embedded in the tubular body such that the embedded length of the supply lines are circumferentially spaced apart from each other within the tubular body and the embedded length of each of the supply lines extends parallel to the longitudinal sensor axis and wherein each of the electrode rings mounted on the tubular body is coupled to a separate supply line and wherein each of the electrode groups includes at least one working electrode and at least one further electrode selected from a counterelectrode and/or a reference electrode positioned on the tubular body in a longitudinally sequential pattern of electrode rings, with each of the electrode groups having the same longitudinally sequential pattern of electrode rings and wherein the implantable sensor produces a signal indicative of analyte concentration when implanted and wherein the plurality of electrode groups are arranged sequentially along the longitudinal sensor axis such that the at least two electrode rings forming each one of the electrode groups are positioned along a continuous longitudinal length of the tubular body which is non-overlapping and separate from the longitudinal length of the tubular body on which the electrode rings of the other electrode groups are positioned; and wherein when an actuation and evaluation unit actuates one of the plurality of electrode groups to obtain a signal indicative of an analyte concentration, the actuation and evaluation unit additionally subjects to an electrical potential the electrode groups which are longitudinally adjacent to the one electrode group being used to obtain the signal indicative of an analyte concentration to shield the electrode group being used to obtain the signal indicative of the analyte concentration.

2. The implantable sensor of claim 1 wherein the electrode rings are electrically connected to the supply lines by electrically plated through-holes that extend at least partially through the tubular body.

3. The implantable sensor of claim 1 wherein electrical contacts for the contacting of the electrode rings are provided at an end of the sensor element directed away from the implantation end.

4. The implantable sensor of claim 1 wherein the electrode rings, on a side directed away from the tubular body, are at least partially surrounded by at least one membrane layer, and wherein the at least one membrane layer is at least partially permeable to the at least one analyte.

5. The implantable sensor of claim 1 wherein the embedded length of the supply lines extend to the implantation end of the tubular body whereby the tubular body does not fully cover the supply lines at the implantation end of the tubular body and wherein the implantation end of the tubular body is coated by an electrical insulation material which electrically insulates the individual supply lines from one another and from the body tissue at the implantation end of the tubular body.

6. The implantable sensor of claim 1 further comprising an implantation needle which is mounted slidably in the tubular body in such a way that the implantation needle, after implantation of the implantable sensor in the medium, can be at least partially withdrawn from the tubular body.

7. The implantable sensor of claim 6 wherein the implantation needle is an acupuncture needle having a diameter of between 0.40 mm and 0.7 mm.

8. The implantable sensor of claim 6 wherein the implantation needle is a needle with a tip which is made at least partially of a biocompatible, enzymatically degradable material, such that the tip becomes at least partially rounded after implantation in the medium.

9. A sensor system for determining a concentration of at least one analyte in a medium, the sensor system comprising at least one of the implantable sensors of claim 1, and further comprising an actuation and evaluation unit which is connected to the electrode rings and which is configured to carry out an electrochemical measurement in order to determine the concentration of the analyte.

10. The implantable sensor of claim 1 wherein six to fifteen supply lines are embedded within the tubular body and are each respectively connected to a separate electrode ring disposed on the tubular body.

11. A method for producing an implantable sensor adapted for determining a concentration of at least one analyte in a medium, comprising:
producing a tubular body for a tubular sensor element wherein the tubular sensor element defines a longitudinal sensor axis;
applying to the tubular body a plurality of electrode groups, each electrode group having at least two electrode rings at longitudinally spaced apart locations, the at least two electrode rings of each electrode group being adapted for electrochemical determination of the concentration of the analyte wherein the at least two electrode rings of each electrode group comprise at least one working electrode and at least one further electrode selected from a counterelectrode and/or a reference electrode and wherein the electrode rings forming the plurality of electrode groups are arranged such that the at least one working electrode and the at least one further electrode of each electrode group defines a longitudinally sequential pattern of electrode rings with each of the electrode groups defining the same longitudinal sequential pattern of electrode rings and wherein the at least two electrode rings forming each one of the electrode groups are positioned along a continuous longitudinal length of the tubular body which is non-overlapping and separate from the longitudinal length of the tubular body on which the electrode rings of the other electrode groups are positioned; and
embedding electrically and/or galvanically insulated supply lines for the at least two electrode rings of each electrode group in the tubular body such that the supply lines have an embedded length that extends parallel to the longitudinal sensor axis and from proximate an end of the tubular element opposite from an implantation end to a respective one of the electrode rings and wherein the supply lines are circumferentially spaced apart from each other within the tubular body, and connecting each of the electrode rings to a separate supply line wherein each of the electrode groups independently produces a signal indicative of analyte concentration when implanted; and
providing an actuation and evaluation unit to actuate one of the plurality of electrode groups to obtain a signal indicative of an analyte concentration, the actuation and evaluation unit additionally configured to subject to an electrical potential the electrode groups which are longitudinally adjacent to the one electrode group being used to obtain the signal indicative of an analyte concentration to shield the electrode group being used to obtain the signal indicative of the analyte concentration.

12. The method of claim 11 wherein the embedding takes place in one method step with the production of the tubular body.

13. The method of claim 11 wherein a plated through-hole is produced in order to connect the electrode rings electrically to the supply lines.

14. The method of claim 13 wherein the plated through-hole is produced by creating a via through at least one material layer between the electrode rings and the supply lines, and wherein the via is then at least partially filled with at least one electrically conductive material.

15. The method of claim 11 wherein, in order to produce the electrode rings, in each case at least one electrically conductive contact ring directed toward the tubular body is first created, and then in each case at least one function layer is applied to the contact ring.

16. The method of claim 15 wherein the contact rings and/or the function layers are applied using in each case at least one of the following methods for structured application of a layer: a laminating method, a spray-on method, an inkjet method, a contact printing method, an offset method, or an electrostatic printing method.

17. The method of claim 15 wherein the application of the contact rings and/or of the function layers involves at least one contact ring and/or at least one function layer being applied to a flexible carrier substrate, and the flexible carrier substrate then being applied to the tubular body.

18. The method of claim 11, further comprising:
surrounding at least partially the electrode rings, on the side directed away from the tubular body, with at least one membrane layer, wherein the at least one membrane layer is at least partially permeable to the at least one analyte.

19. The method of claim 11 wherein between 6 and 15 supply lines are embedded within the tubular body and are each respectively connected to a separate electrode ring disposed on the tubular body.

20. The method of claim 11 wherein the embedded length of the supply lines extend to the implantation end of the tubular body and, wherein after the step of embedding the supply lines, the supply lines are exposed at the implantation end of the tubular body and the method further comprises:
electrically insulating the individual supply lines from one another and from the body tissue at the implantation end of the tubular body by coating the implantation end of the tubular body with an electrical insulation material.

21. The method of claim 11, further comprising:
introducing an implantation needle into the tubular body.

22. The method of claim 11 wherein the embedded length of the supply lines extend to the implantation end of the tubular body and, after the step of embedding the supply lines, the supply lines are exposed at the implantation end of the tubular body and wherein the method further comprises coating the implantation end of the tubular body to thereby electrically insulate the exposed supply lines from one another and from the body tissue at the implantation end of the tubular body.

23. An implantable sensor for determining a concentration of at least one analyte in a medium, the implantable sensor comprising a flexible, tubular sensor element, the tubular sensor element defining a longitudinal sensor axis, and the tubular sensor element comprising a flexible, tubular body wherein a plurality of electrode groups are disposed on the tubular body, each electrode group including at least two electrode rings adapted for electrochemical determination of the concentration of the analyte are mounted on the tubular body, the at least two electrode rings of each electrode group being longitudinally spaced apart, said electrode rings of each electrode group comprising at least one working electrode and at least one further electrode selected from a counter electrode and/or a reference electrode, wherein electrically and/or galvanically insulated supply lines for the at least two electrode rings of each electrode group are embedded in the tubular body, and wherein the supply lines have an embedded length that extends parallel to the longitudinal axis and from proximate an end of the sensor element opposite from an implantation end to a respective one of the electrode rings and wherein the supply lines are circumferentially spaced apart from each other within the tubular body, wherein each electrode group of the implantable sensor independently produces a signal indicative of analyte concentration when implanted and wherein the electrode rings forming the plurality of electrode groups are arranged such that the at least one working electrode and the at least one further electrode of each electrode group defines a longitudinally sequential pattern of electrode rings with each of the electrode groups defining the same longitudinal sequential pattern of electrode rings and wherein the at least two electrode rings forming each one of the electrode groups are positioned along a continuous longitudinal length of the tubular body which is non-overlapping and separate from the longitudinal length of the tubular body on which the electrode rings of the other electrode groups are positioned; and     an actuation and evaluation unit operably connected with the implantable sensor wherein the actuation and evaluation unit actuates and evaluates the plurality of electrode groups independently of each other;

wherein when the actuation and evaluation unit actuates one of the plurality of electrode groups to obtain a signal indicative of an analyte concentration, the actuation and evaluation unit additionally subjects to an electrical potential the electrode groups which are longitudinally adjacent to the one electrode group being used to obtain the signal indicative of the analyte concentration to shield the electrode group being used to obtain the signal indicative of the analyte concentration.

24. The implantable sensor of claim 23 wherein each electrode group includes three electrode rings comprising a working electrode, a counter electrode and a reference electrode.

25. The implantable sensor of claim 23 wherein, when the actuation and evaluation unit actuates one of the plurality of electrode groups to obtain a signal indicative of an analyte concentration, the actuation and evaluation unit subjects to an electrical potential the electrode rings which are longitudinally adjacent to the one electrode group being used to obtain the signal indicative of an analyte concentration.

26. The implantable sensor of claim 25 wherein six to fifteen supply lines are embedded within the tubular body and are each respectively connected to a separate electrode ring disposed on the tubular body and wherein the embedded length of the supply lines extend to the implantation end of the tubular body whereby the tubular body does not fully cover the supply lines at the implantation end of the tubular body and wherein the implantation end of the tubular body is coated by an electrical insulation material which electrically insulates the individual supply lines from one another and from the body tissue at the implantation end of the tubular body.

27. The implantable sensor of claim 25 wherein each of the electrode rings extend about a complete circumference of the tubular body.

\* \* \* \* \*